US012605147B2

(12) United States Patent
Okuda

(10) Patent No.: US 12,605,147 B2
(45) Date of Patent: Apr. 21, 2026

(54) ULTRASOUND DIAGNOSTIC APPARATUS AND PROGRAM, CONFIGURED FOR CONTINUOUSLY CAPTURING IMAGES FOR AN IMAGE GROUP, AT A PREDETERMINED TIME INTERVAL OR LESS

(71) Applicant: FUJIFILM Healthcare Corporation, Kashiwa (JP)

(72) Inventor: Yasuo Okuda, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 146 days.

(21) Appl. No.: 18/429,732

(22) Filed: Feb. 1, 2024

(65) Prior Publication Data

US 2024/0277320 A1 Aug. 22, 2024

(30) Foreign Application Priority Data

Feb. 22, 2023 (JP) ................................. 2023-026065

(51) Int. Cl.
*A61B 8/00* (2006.01)
*G06T 11/60* (2006.01)
*G16H 30/40* (2018.01)

(52) U.S. Cl.
CPC ................ *A61B 8/54* (2013.01); *A61B 8/463* (2013.01); *A61B 8/469* (2013.01); *A61B 8/481* (2013.01); *G06T 11/60* (2013.01); *G16H 30/40* (2018.01); *G06T 2210/41* (2013.01)

(58) Field of Classification Search
CPC .................................. A61B 8/54; G16H 30/40
See application file for complete search history.

(56) References Cited

U.S. PATENT DOCUMENTS

| | | | |
|---|---|---|---|
| 2006/0058625 A1* | 3/2006 | Mori ....................... | A61B 8/463 |
| | | | 600/407 |
| 2014/0063011 A1* | 3/2014 | Noshi .................. | H04N 13/282 |
| | | | 345/420 |
| 2025/0308029 A1* | 10/2025 | Ando ..................... | A61B 8/469 |

FOREIGN PATENT DOCUMENTS

| | | |
|---|---|---|
| JP | 2006-014989 A | 1/2006 |
| JP | 2008-237758 A | 10/2008 |

* cited by examiner

*Primary Examiner* — Shivang I Patel
(74) *Attorney, Agent, or Firm* — Paul Teng

(57) ABSTRACT

An ultrasound diagnostic apparatus enables a user to easily select a target image from among a plurality of images captured by an image diagnostic apparatus. An identification unit identifies, as one image group, a plurality of images continuously captured at time intervals equal to or less than a predetermined time interval among a plurality of images captured by an image diagnostic apparatus. A display controller displays, on a display, the image group and an image other than the image group in a distinguishable manner. For example, the display controller displays the image group as one thumbnail image on the display, and displays the image other than the image group as one thumbnail image on the display.

10 Claims, 14 Drawing Sheets

ULTRASOUND DIAGNOSTIC APPARATUS AND PROGRAM, CONFIGURED FOR CONTINUOUSLY CAPTURING IMAGES FOR AN IMAGE GROUP, AT A PREDETERMINED TIME INTERVAL OR LESS

CROSS-REFERENCE TO RELATED APPLICATION

The present application claims priority from Japanese patent application 2023-026065 filed with the Japanese Patent Office on Feb. 22, 2023, the content of which is hereby incorporated by reference into this application.

BACKGROUND OF THE INVENTION

1. Field of the Invention

The present invention relates to a technique of displaying a plurality of images in a distinguishable manner in an image diagnostic apparatus, such as an ultrasound diagnostic apparatus.

2. Description of the Related Art

In an image diagnostic apparatus, such as an ultrasound diagnostic apparatus, an X-ray computed tomography (CT) apparatus, a magnetic resonance imaging (MRI) apparatus, or an X-ray diagnostic apparatus, an image generated by another image diagnostic apparatus or an image stored in an image server may be acquired.

JP2006-14989A describes an apparatus that displays each thumbnail image in a group in accordance with an examination item or an examination content.

JP2008-237758A describes an apparatus that collects a plurality of diagnostic images, sets group information in accordance with a classification of an examination, and adds the group information to the diagnostic images and saves the diagnostic images with the group information in a case in which an instruction to save the diagnostic images is given.

SUMMARY OF THE INVENTION

In a case in which the image diagnostic apparatus acquires the image, it is conceivable that a list of pieces of information related to an image that is an acquisition candidate is displayed as text information, and a user selects the image that is the acquisition candidate with reference to the list. However, it is a burden on the user to select the image that is the acquisition candidate only from the text information. In addition, in a case in which a contrast examination is performed, information related to a time phase in which an image is captured is generally useful information for selecting the image that is the acquisition candidate. However, in a case in which the information related to the time phase is not presented to the user, it is difficult for the user to select the image that is the acquisition candidate.

An object of the present invention is to enable a user to easily select a target image from among a plurality of images captured by an image diagnostic apparatus.

An aspect of the present invention relates to an ultrasound diagnostic apparatus including: an identification unit that identifies, as one image group, a plurality of images continuously captured at time intervals equal to or less than a predetermined time interval among a plurality of images captured by an image diagnostic apparatus; and a controller that displays, on a display, the image group and an image other than the image group in a distinguishable manner.

In the configuration described above, the image diagnostic apparatus is, for example, an ultrasound diagnostic apparatus, an X-ray CT apparatus, an MRI apparatus, or an X-ray diagnostic apparatus. The image may be an image stored in the image diagnostic apparatus, or may be an image stored in an apparatus, such as an image server. The predetermined time interval may be changed by the user. For example, a time interval in which it is assumed that a plurality of images continuously captured can constitute one image group may be set as the predetermined time interval. For example, the images are displayed in an aspect in which the images included in the image group and the image other than the image group can be identified from each other. The images included in the image group may be collectively displayed such that the user recognizes that the images included in the image group constitute one group. The ultrasound diagnostic apparatus may be formed as a single apparatus or may be formed of a plurality of apparatuses. Identification processing via the identification unit and display control via the controller may be realized by a single apparatus or may be realized by a plurality of apparatuses.

The identification unit may identify the image group by assuming that the images included in the image group are images generated by imaging a subject using a contrast medium.

The controller may display, on the display, the image group as one thumbnail image.

In a case in which the thumbnail image representing the image group is selected by a user, the controller may display, on the display, a dialog for selecting an image that is an acquisition candidate, the dialog may be an image in which figures respectively corresponding to the images included in the image group are arranged and represented in accordance with an order of imaging times of the images, and in a case in which the figure is selected on the dialog, the controller may determine the image corresponding to the selected figure as the image that is the acquisition candidate.

In a case in which the image group is displayed as one thumbnail image after the image that is the acquisition candidate is determined, the controller may display, on the display, the image that is the acquisition candidate and the image group as separate thumbnail images such that a fact that the image that is the acquisition candidate is an image belonging to the image group is indicated.

In a case in which a thumbnail image representing the image that is the acquisition candidate is displayed on the display and the thumbnail image representing the image that is the acquisition candidate is selected, the controller may determine the image that is the acquisition candidate corresponding to the selected thumbnail image as an image that is not the acquisition candidate.

The dialog may have a shape in which the figures are disposed in an annular shape in accordance with the imaging times of the images.

The controller may dispose the figures with a gap between a figure corresponding to an image having an earliest imaging time in the image group and a figure corresponding to an image having a latest imaging time in the image group.

Based on a timing at which the contrast medium flows in a specific part of the subject, the controller may display, in the dialog, a figure corresponding to an image captured at the timing in a distinguishable manner from figures corresponding to other images.

Another aspect of the present invention relates to a program causing a computer to function as: an identification unit that identifies, as one image group, a plurality of images continuously captured at time intervals equal to or less than a predetermined time interval among a plurality of images captured by an image diagnostic apparatus; and a controller that displays, on a display, the image group and an image other than the image group in a distinguishable manner.

The aspects of the present invention enable the user to easily select the target image from among a plurality of images captured by the image diagnostic apparatus.

DESCRIPTION OF THE PREFERRED EMBODIMENTS

Figure 1:
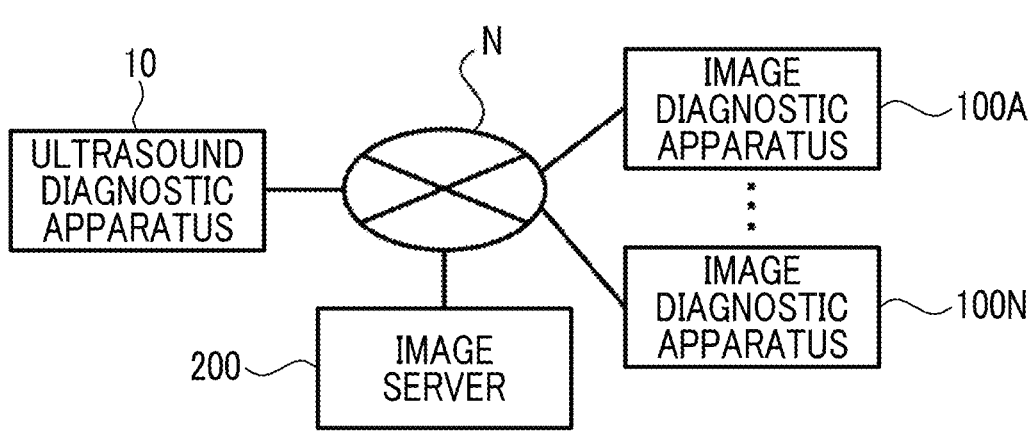
FIG. 1 is a block diagram showing a configuration of an image diagnostic system according to an embodiment.

An image diagnostic system according to an embodiment will be described with reference to FIG. 1. FIG. 1 shows a configuration of the image diagnostic system according to the embodiment.

The image diagnostic system includes an ultrasound diagnostic apparatus 10 and one or more image diagnostic apparatuses (for example, image diagnostic apparatuses 100A, . . . , and 100N). Each of the image diagnostic apparatuses 100A, . . . , and 100N is an ultrasound diagnostic apparatus, an X-ray computed tomography (CT) apparatus, a magnetic resonance imaging (MRI) apparatus, or an X-ray diagnostic apparatus. Hereinafter, in a case in which it is not necessary to distinguish between the image diagnostic apparatuses 100A, . . . , and 100N, the image diagnostic apparatuses 100A, . . . , and 100N are referred to as "image diagnostic apparatus 100". Image data (that is, ultrasound image data) is generated by imaging via the ultrasound diagnostic apparatus 10. Image data (for example, CT image data or MRI image data) is generated by imaging via the image diagnostic apparatus 100. Hereinafter, the image data will be referred to as an image.

Accessory information including patient information and examination information is associated with the image. The patient information is information for identifying a patient, and includes, for example, a patient ID, information indicating a name of the patient, information indicating a date of birth of the patient, and information indicating the gender of the patient. The examination information includes information for identifying an examination (for example, an examination ID), apparatus identification information for identifying the image diagnostic apparatus 100 that captures the image, imaging time information indicating a time (for example, date and time) when the image is captured, information indicating an imaged part, and imaging condition information indicating an imaging condition. For example, information conforming to a DICOM standard is associated with the image as the accessory information. For example, in a case in which the image is generated by imaging via the ultrasound diagnostic apparatus 10, the accessory information is associated with the image by the ultrasound diagnostic apparatus 10. In the same manner, in a case in which the image is generated by imaging via the image diagnostic apparatus 100, the accessory information is associated with the image by the image diagnostic apparatus 100.

The ultrasound diagnostic apparatus 10 and each image diagnostic apparatus 100 have a function of communicating with other apparatuses. The communication may be wired communication or wireless communication. As the wireless communication, for example, short-range wireless communication, Wi-Fi (registered trademark), or the like is used. Wireless communication of standards other than these examples may be used. For example, the ultrasound diagnostic apparatus 10 and each image diagnostic apparatus 100 communicate with each other through a communication path N, such as a local area network (LAN) or the Internet. The ultrasound diagnostic apparatus 10 and each image diagnostic apparatus 100 may communicate with each other through an external apparatus, such as a server.

The image diagnostic system may include an image server 200. The image server 200 has a function of communicating with other apparatuses. For example, the image generated by imaging via the image diagnostic apparatus 100 is transmitted to the image server 200 through the communication path N and then stored in the image server 200. In the same manner, the image generated by imaging via the ultrasound diagnostic apparatus 10 may be transmitted to the image server 200 through the communication path N and then stored in the image server 200. It should be noted that the image generated by the image diagnostic apparatus 100 may be stored in the image diagnostic apparatus 100 itself. In the same manner, the image generated by the ultrasound diagnostic apparatus 10 may be stored in the ultrasound diagnostic apparatus 10 itself.

The image stored in the image server 200 may be transmitted to the ultrasound diagnostic apparatus 10 or the image diagnostic apparatus 100. For example, the image generated by the image diagnostic apparatus 100 is stored in the image server 200, and the image is transmitted from the image server 200 to the ultrasound diagnostic apparatus 10 in accordance with an instruction (for example, an import instruction) for transmission to the ultrasound diagnostic apparatus 10.

The image may be transmitted and received between the apparatuses without going through the image server 200. For example, the image generated by the image diagnostic apparatus 100 may be transmitted to the ultrasound diagnostic apparatus 10. In the same manner, the image generated by the ultrasound diagnostic apparatus 10 may be transmitted to the image diagnostic apparatus 100.

For example, it is conceivable that a user refers to the image generated by imaging via the image diagnostic apparatus 100 in the ultrasound diagnostic apparatus 10. In this case, the image generated by imaging via the image diagnostic apparatus 100 is transmitted from the image diagnostic apparatus 100 or the image server 200 to the ultrasound diagnostic apparatus 10, and the user refers to the image.

Figure 2:
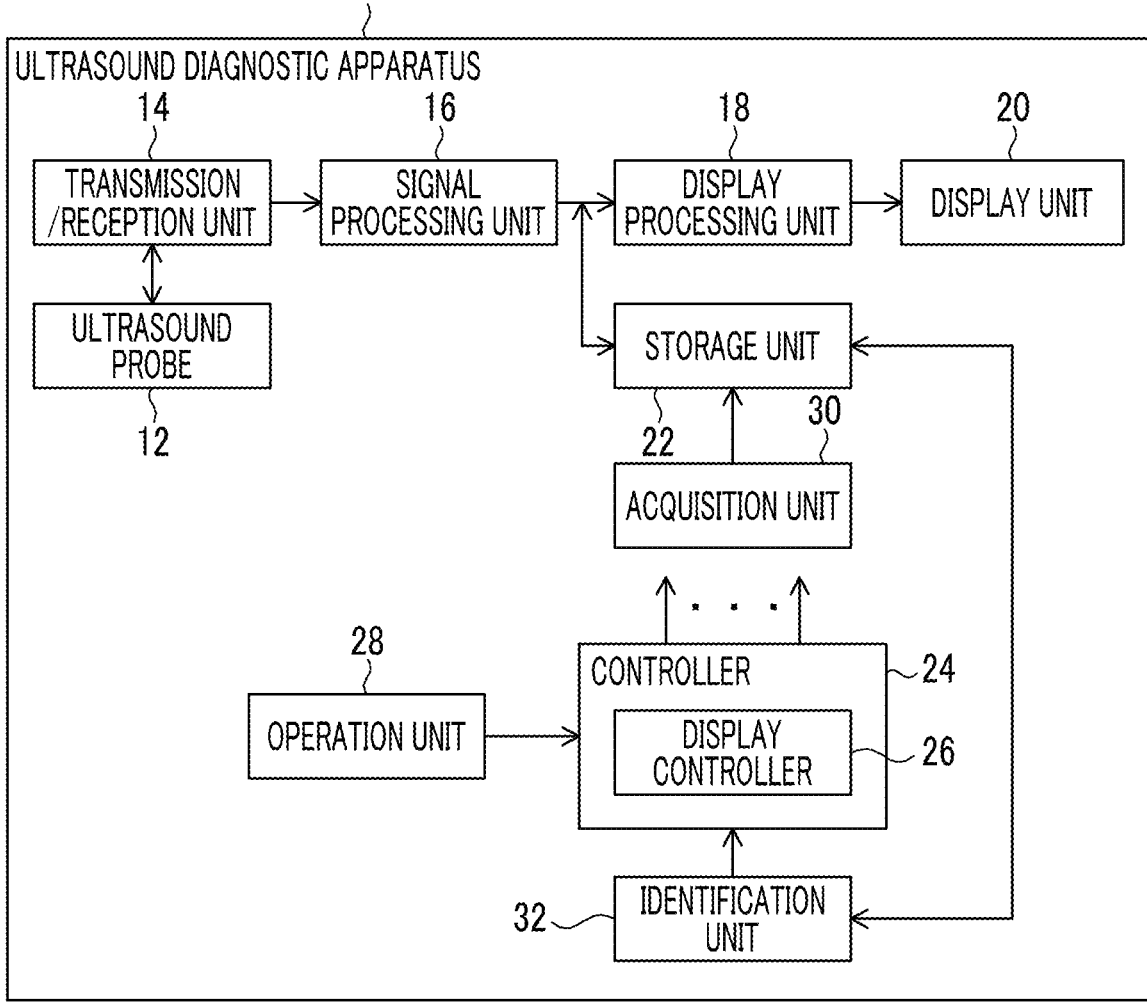
FIG. 2 is a block diagram showing a configuration of an ultrasound diagnostic apparatus according to the embodiment.

The ultrasound diagnostic apparatus 10 according to the embodiment will be described with reference to FIG. 2. FIG. 2 shows a configuration of the ultrasound diagnostic apparatus 10.

The ultrasound diagnostic apparatus 10 generates an ultrasound image by transmitting and receiving ultrasound using an ultrasound probe 12. For example, the ultrasound diagnostic apparatus 10 transmits the ultrasound into a subject and receives the ultrasound reflected from the inside of the subject to generate the ultrasound image representing a tissue inside the subject.

The ultrasound probe 12 is a device that transmits and receives the ultrasound. The ultrasound probe 12 includes, for example, a ID array oscillator. The ID array oscillator is formed by unilaterally arranging a plurality of ultrasound oscillators. An ultrasound beam is formed by the 1D array oscillator, and electron scanning with the ultrasound beam is repeatedly performed. As a result, a scanning surface is formed in a living body for each electron scanning. The scanning surface corresponds to a two-dimensional echo data acquisition space. The ultrasound probe 12 may include, instead of the 1D array oscillator, a 2D array oscillator formed by two-dimensionally arranging a plurality of oscillating elements. In a case in which the ultrasound beam is formed by the 2D array oscillator and the electron scanning with the ultrasound beam is repeatedly performed, the scanning surface as the two-dimensional echo data acquisition space is formed for each electron scanning. In a case in which the scanning with the ultrasound beam is performed two-dimensionally, a three-dimensional space as a three-dimensional echo data acquisition space is formed. As a scanning method, sector scanning, linear scanning, convex scanning, or the like is used.

A transmission/reception unit 14 functions as a transmission beam former and a reception beam former. In the transmission, the transmission/reception unit 14 supplies a plurality of transmission signals having a certain delay relationship to the plurality of ultrasound oscillators included in the ultrasound probe 12. As a result, a transmission beam of the ultrasound is formed. In the reception, a reflection wave (RF signal) from the living body is received by the ultrasound probe 12, whereby a plurality of reception signals are output from the ultrasound probe 12 to the transmission/reception unit 14. The transmission/reception unit 14 forms a reception beam by applying phasing addition processing to the plurality of reception signals. The beam data is output to a signal processing unit 16. That is, the transmission/reception unit 14 forms the reception beam by performing delay processing on the reception signal obtained from each ultrasound oscillator in accordance with a delay processing condition for each ultrasound oscillator and performing addition processing on the plurality of reception signals obtained from the plurality of ultrasound oscillators. The delay processing condition is defined by reception delay data indicating a delay time. A reception delay data set (that is, a set of delay times) corresponding to the plurality of ultrasound oscillators is supplied from a controller 24.

The electron scanning with the ultrasound beam (that is, the transmission beam and the reception beam) is performed by the action of the transmission/reception unit 14, thereby forming the scanning surface. The scanning surface corresponds to a plurality of beam data, which constitute reception frame data (specifically, RF signal frame data). It should be noted that each beam data is formed of a plurality of echo data arranged in a depth direction. By repeating the electron scanning with the ultrasound beam, the plurality of reception frame data arranged on a time axis are output from the transmission/reception unit 14 to the signal processing unit 16. The plurality of reception frame data constitute a reception frame string.

In a case in which the electron scanning with the ultrasound beam is performed two-dimensionally by the action of the transmission/reception unit 14, the three-dimensional echo data acquisition space is formed, and the volume data as an echo data aggregate is acquired from the three-dimensional echo data acquisition space. By repeating the electron scanning with the ultrasound beam, a plurality of volume data arranged on a time axis are output from the transmission/reception unit 14 to the signal processing unit 16. The plurality of volume data constitute a volume data string.

The signal processing unit 16 generates the ultrasound image (for example, a B-mode image) by applying, to the beam data output from the transmission/reception unit 14, signal processing, such as a coordinate transformation function and an interpolation processing function via detection, amplitude compression (amplitude transform) such as logarithmic compression, and a conversion function (digital scan converter (DSC)). It should be noted that the ultrasound image according to the present embodiment is not limited to the B-mode image, and may be a color Doppler image, a pulse Doppler image, a strain image, a shear wave elastography image, or the like.

A display processing unit 18 performs overlay processing of graphic data necessary for the ultrasound image, thereby generating display image data. The display image is output to a display unit 20, and one or more images are arranged and displayed in a display aspect in accordance with a display mode.

The display unit 20 is a display, such as a liquid crystal display or an EL display. The ultrasound image, such as the B-mode image, is displayed on the display unit 20. The display unit 20 may be a device comprising both the display and an operation unit 28. For example, a graphic user interface (GUI) may be realized by the display unit 20. In addition, a user interface, such as a touch panel, may be realized by the display unit 20.

A storage unit 22 constitutes one or more storage areas for storing data. The storage unit 22 is, for example, a hard disk drive (HDD), a solid state drive (SSD), various types of memories (for example, RAM, DRAM, or ROM), other storage devices (for example, optical disk), or a combination thereof. The storage unit 22 stores the image generated by imaging via the ultrasound diagnostic apparatus 10, the image acquired from the image diagnostic apparatus 100, the information indicating the imaging condition, the information related to the patient, and the like.

The controller 24 controls an operation of each unit of the ultrasound diagnostic apparatus 10.

The controller 24 includes a display controller 26. The display controller 26 displays the image on the display unit 20. The display controller 26 may display the image generated by imaging via the ultrasound diagnostic apparatus 10 on the display unit 20, or may display the image acquired from the image diagnostic apparatus 100 on the display unit 20. Display control via the display controller 26 will be described in detail below. It should be noted that a part or all of functions of the display processing unit 18 may be included in the display controller 26.

The operation unit 28 is a device for the user to input a condition, a command, and the like necessary for imaging into the ultrasound diagnostic apparatus 10. For example, the operation unit 28 is an operation panel, a switch, a button, a keyboard, a mouse, a track ball, or a joystick.

An acquisition unit 30 acquires the image from the image diagnostic apparatus 100 or the image server 200. For example, in a case in which a search condition is designated by a user, the acquisition unit 30 acquires the image that coincides with the search condition. The acquisition unit 30 may acquire only the accessory information of the image, or may acquire the image with which the accessory information is associated.

An identification unit 32 identifies, as one image group, a plurality of images continuously captured at time intervals equal to or less than a predetermined time interval among a plurality of images captured by the image diagnostic apparatuses 100 (that is, a plurality of images generated by imaging via the image diagnostic apparatuses 100). For example, a plurality of images are acquired by the acquisition unit 30, and the identification unit 32 identifies, as one image group, a plurality of images continuously captured at the time intervals equal to or less than the predetermined time interval among a plurality of acquired images.

For example, in a case in which a contrast examination (imaging performed by injecting a contrast medium into the patient) is performed by the image diagnostic apparatus 100, in general, a plurality of images representing the subject in a state in which the contrast medium is injected are continuously captured. For example, a plurality of images representing a state in which the contrast medium flows in a blood vessel are continuously captured. As described above, in the contrast examination, a plurality of images are continuously captured at the time intervals equal to or less than the predetermined time interval. It is presumed that the image group (that is, a plurality of images continuously captured at the time intervals equal to or less than the predetermined time interval) is an image group representing the subject in a state in which the contrast medium is injected. The identification unit 32 identifies the image group by assuming that the images included in the image group continuously captured at the time intervals equal to or less than the predetermined time interval are images generated by imaging the patient using the contrast medium (that is, images representing the subject in a state in which the contrast medium is injected).

The display controller 26 displays, on the display unit 20, the image group identified by the identification unit 32 and an image other than the image group in a distinguishable manner. That is, the display controller 26 displays, on the display unit 20, a plurality of images continuously captured at the time intervals equal to or less than the predetermined time interval and an image that does not satisfy such a condition in a distinguishable manner.

For example, the display controller 26 displays, on the display unit 20, each of a plurality of images acquired by the acquisition unit 30 as thumbnail images. In addition, the display controller 26 collectively displays, on the display unit 20, the image group identified by the identification unit 32 as one thumbnail image. That is, the display controller 26 collectively displays a plurality of images identified as one image group by the identification unit 32 as one thumbnail image on the display unit 20, and displays the thumbnail images of the images other than the image group as individual images on the display unit 20.

For example, in a case in which the contrast examination is performed, the thumbnail images of a plurality of images collected as one image group are the thumbnail images of the image group presumed to represent the subject in a state in which the contrast medium is injected. The display controller 26 displays the thumbnail image of such an image group and the thumbnail image of the image other than the image group in a distinguishable manner. Then, the user can recognize the thumbnail image of the image group representing the subject in a state in which the contrast medium is injected, and the thumbnail image of the image other than the image group in a distinguishable manner.

Figure 3:
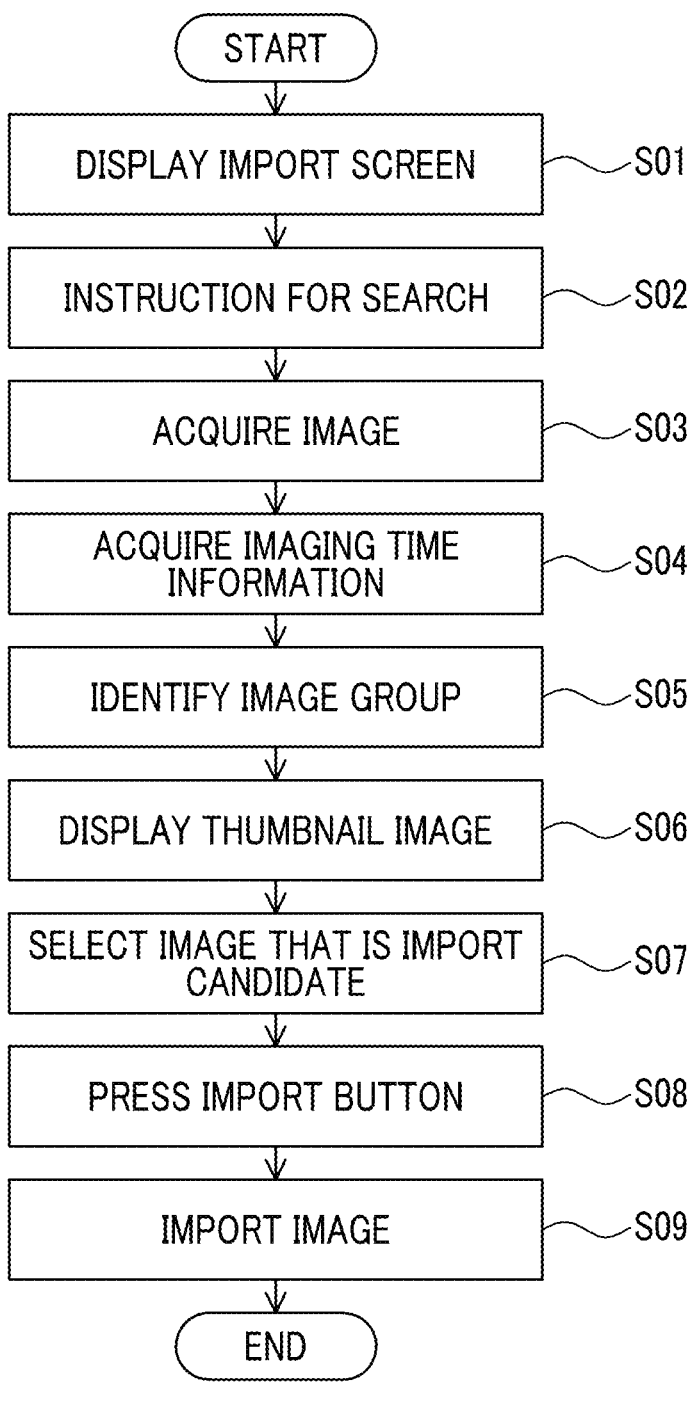
FIG. 3 is a flowchart showing a flow of processing via the ultrasound diagnostic apparatus according to the embodiment.

Hereinafter, processing in which the ultrasound diagnostic apparatus 10 acquires the image generated by the image diagnostic apparatus 100 will be described with reference to FIG. 3. As an example, the ultrasound diagnostic apparatus 10 acquires the image from the image server 200.

First, the user operates the operation unit 28 to give an instruction to display an import screen (S01). For example, an input field for the search condition and the like are displayed on the import screen. The search condition is a condition for searching for the image to be acquired.

Next, the user inputs the search condition on the import screen and gives an instruction for the search (S02). For example, the patient information or the like is input as the search condition.

The acquisition unit 30 searches the image server 200 for the image that coincides with the input search condition, and acquires the image that coincides with the search condition (S03). The accessory information is associated with the acquired image. Here, a plurality of images are acquired by the acquisition unit 30. Each image is temporarily acquired in this stage.

The identification unit 32 acquires the imaging time information from the accessory information of each image acquired by the acquisition unit 30 (S04). The identification unit 32 refers to the imaging time information of each image to identify, as one image group, a plurality of images continuously captured at the time intervals equal to or less than the predetermined time interval among a plurality of images acquired by the acquisition unit 30 (S05).

The display controller 26 displays, on the display unit 20, each image acquired by the acquisition unit 30 as the thumbnail image (S06). In this case, the display controller 26 displays, on the display unit 20, the thumbnail image of the image group identified by the identification unit 32 and the thumbnail image of the image other than the image group in a distinguishable manner.

The user selects an image that is an import candidate by selecting the thumbnail image from among the plurality of displayed thumbnail images (S07). The user may select the thumbnail image of the image group or may select the thumbnail image of the image other than the image group.

In a case in which the user presses an import button displayed on the display unit 20 (S08), the acquisition unit 30 imports the image that is the import candidate or the image group from the image server 200 into the ultrasound diagnostic apparatus 10 (S09). The storage unit 22 of the ultrasound diagnostic apparatus 10 stores the acquired image or image group. The acquired image or image group is registered in a database constructed by the ultrasound diagnostic apparatus 10.

In a case in which the user gives an instruction to terminate the image import processing, the import screen is closed.

As described above, by displaying the image group continuously captured at the time intervals equal to or less than the predetermined time interval and the image other than the image group in a distinguishable manner, the user can recognize the image group and the image other than the image group in a distinguishable manner. For example, the user can recognize the image group representing a state in which the contrast medium is injected into the subject and one or more images representing a state in which the contrast medium is not injected into the subject in a distinguishable manner.

Hereinafter, the embodiment will be described in detail with reference to a specific example.

Figure 4:
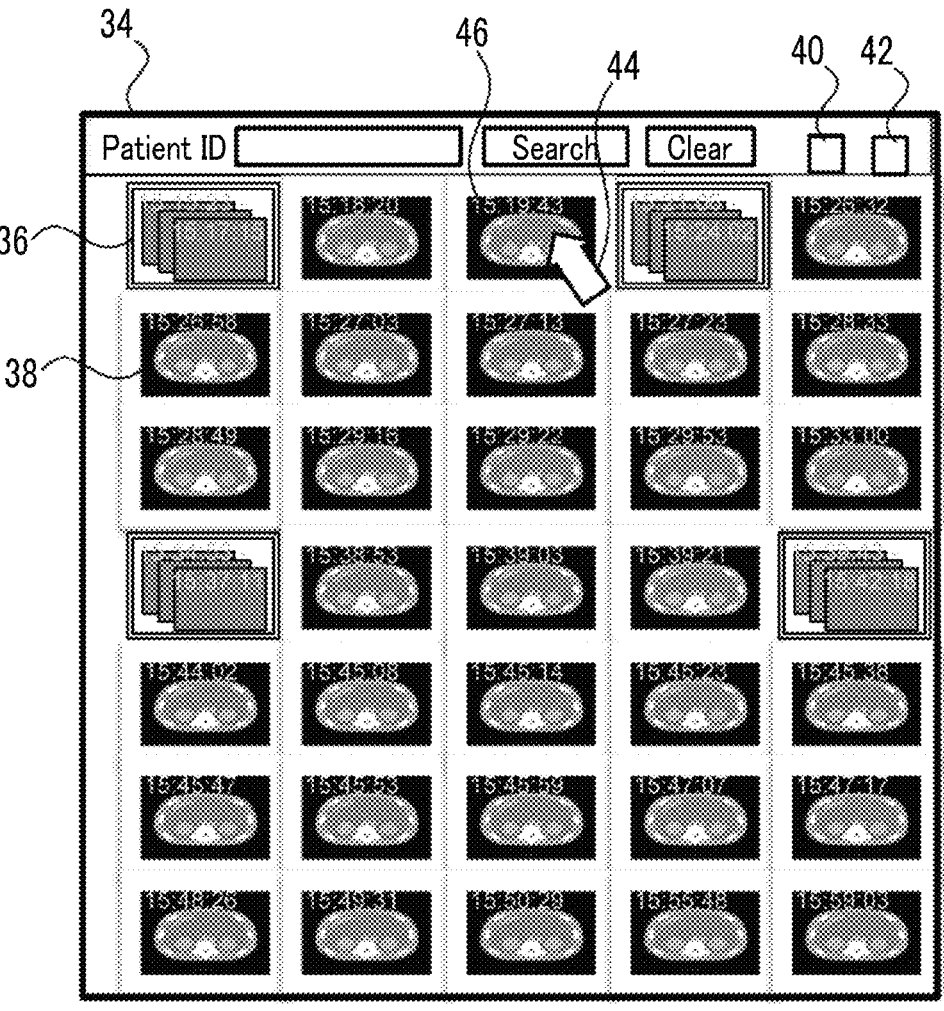
FIG. 4 is a diagram showing an import screen.

The import screen will be described with reference to FIG. 4. FIG. 4 shows an import screen 34.

In a case in which the instruction to display the import screen 34 is given by the user, the display controller 26 displays the import screen 34 on the display unit 20.

The display controller 26 displays one or more thumbnail images 36 and one or more thumbnail images 38 on the import screen 34. The thumbnail image 36 is a thumbnail image collectively representing the image group identified by the identification unit 32. For example, the thumbnail image 36 is a thumbnail image collectively representing the image group presumed to represent the subject in a state in which the contrast medium is injected. For example, the thumbnail image 36 is a thumbnail image in which a plurality of images included in the image group are super-imposed and represented in an order of the imaging times. The thumbnail image 38 is a thumbnail image representing one image which is not included in the image group iden-tified by the identification unit 32. For example, the thumb-nail image 38 is a thumbnail image representing the image presumed to represent the subject in a state in which the contrast medium is not injected.

In a case in which the search condition is input and the image is searched for in step S02, one or more thumbnail images 36 and one or more thumbnail images 38 are displayed on the import screen 34 as the result of the search.

For example, an input field for the patient ID is displayed on the import screen 34. In a case in which the user inputs the patient ID into the input field and gives the instruction for the search, the acquisition unit 30 searches for and acquires a plurality of images associated with the input patient ID on the image server 200. The identification unit 32 identifies, as one image group, a plurality of images con-tinuously captured at the time intervals equal to or less than the predetermined time interval among a plurality of images acquired in this way. The display controller 26 displays the identified image group as one thumbnail image 36 on the import screen 34, and displays the unidentified image as one thumbnail image 38 on the import screen 34.

Expansion buttons 40 and 42 may be displayed on the import screen 34. The expansion button 40 is a button for designating a storage location (for example, a medium) to be searched. In a case in which the expansion button 40 is pressed, a screen for selecting the storage location to be searched is displayed. The image is searched for from the storage location selected on the screen. The expansion button 42 is a button for designating the search condition. In a case in which the expansion button 42 is pressed, a list of input fields for inputting the search conditions is displayed. The image is searched for in accordance with the condition input into the input field.

The user selects the image to be imported by selecting the thumbnail image displayed on the import screen 34. For example, a pointer 44 for selecting the thumbnail image is displayed on the import screen 34. The user operates the pointer 44 to select the thumbnail image.

In the example shown in FIG. 4, a thumbnail image 46 is selected. The thumbnail image 46 is a thumbnail image representing the image that is not included in the image group. It should be noted that, in a case in which the import screen 34 is displayed on a touch panel display, a thumbnail image of the image to be imported may be selected by a touch operation.

Figure 5:
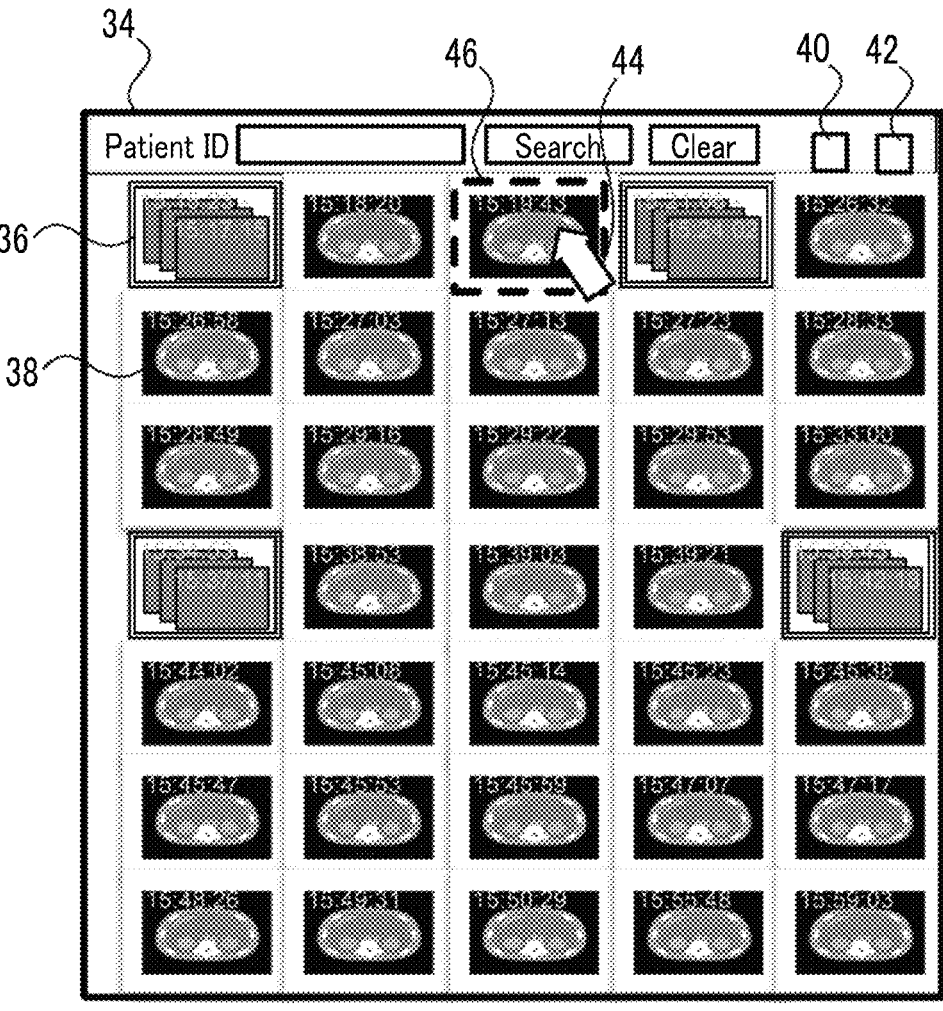
FIG. 5 is a diagram showing the import screen.

In a case in which the thumbnail image 46 representing the image to be imported is selected, as shown in FIG. 5, the display controller 26 may display, on the import screen 34, a frame or the like visually indicating that the thumbnail image 46 is selected. For example, a frame surrounding the selected thumbnail image 46 is displayed on the import screen 34.

In a case in which the user selects the thumbnail image 46 and gives an instruction to import the image, the acquisition unit 30 imports the image represented by the thumbnail image 46 from the image server 200 into the ultrasound diagnostic apparatus 10. The imported image is stored in the storage unit 22. For example, in a case in which the import button is displayed on the import screen 34 and the import button is pressed, the acquisition unit 30 imports the image represented by the thumbnail image 46 from the image server 200. The display controller 26 may display the imported image on the display unit 20.

Hereinafter, processing of selecting the thumbnail image representing the image group and importing the image group will be described with reference to FIGS. 6 to 14.

Figure 6:
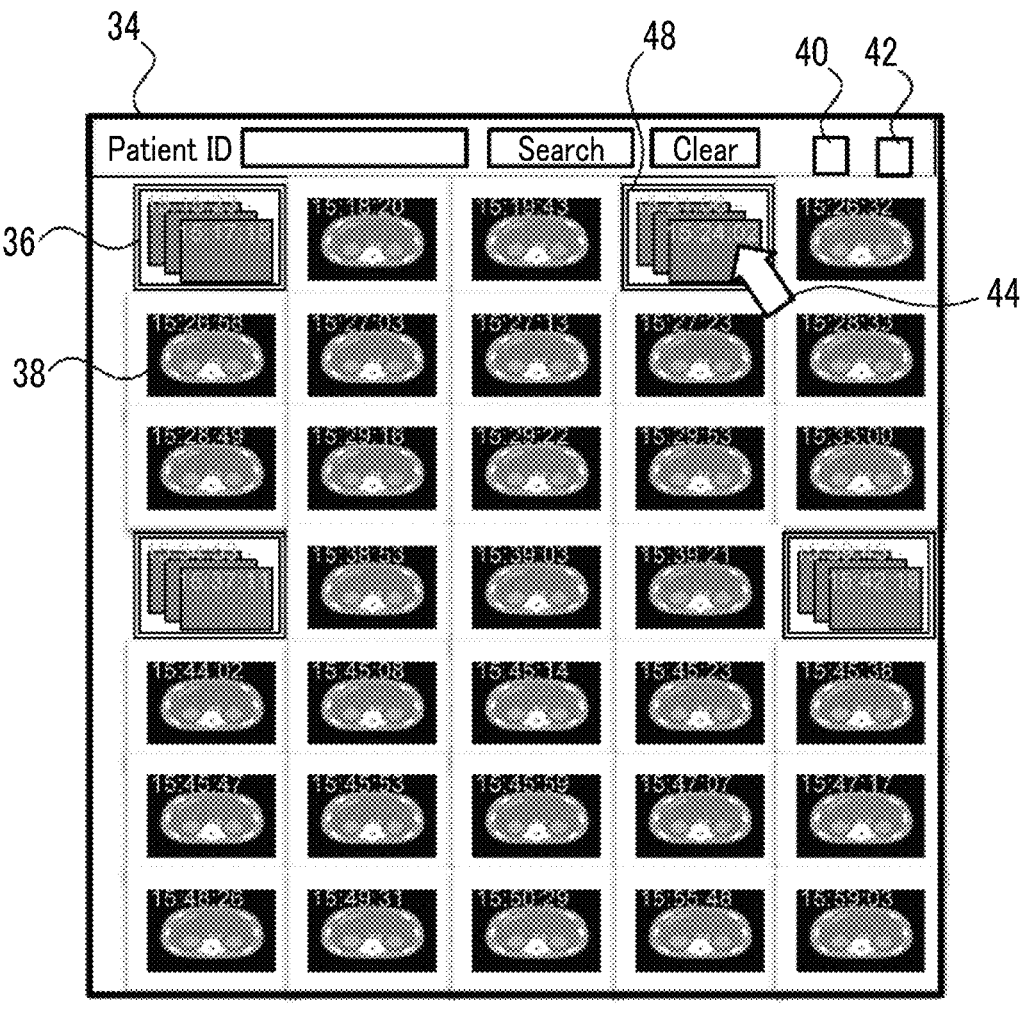
FIG. 6 is a diagram showing the import screen.

FIG. 6 shows the import screen 34. Here, a thumbnail image 48 representing a certain image group is selected by the user using the pointer 44. For convenience of descrip-tion, the image group represented by the thumbnail image 48 will be referred to as "image group A". For example, the user operates the mouse included in the operation unit 28 to click the mouse in a state in which the thumbnail image 48 is designated by using the pointer 44. As a result, the thumbnail image 48 is selected.

In a case in which the thumbnail image 48 representing the image group A is selected by the user, the display controller 26 displays, on the display unit 20, a dialog for selecting an image that is an acquisition candidate (that is, the import candidate) from the image group A.

Figure 7:
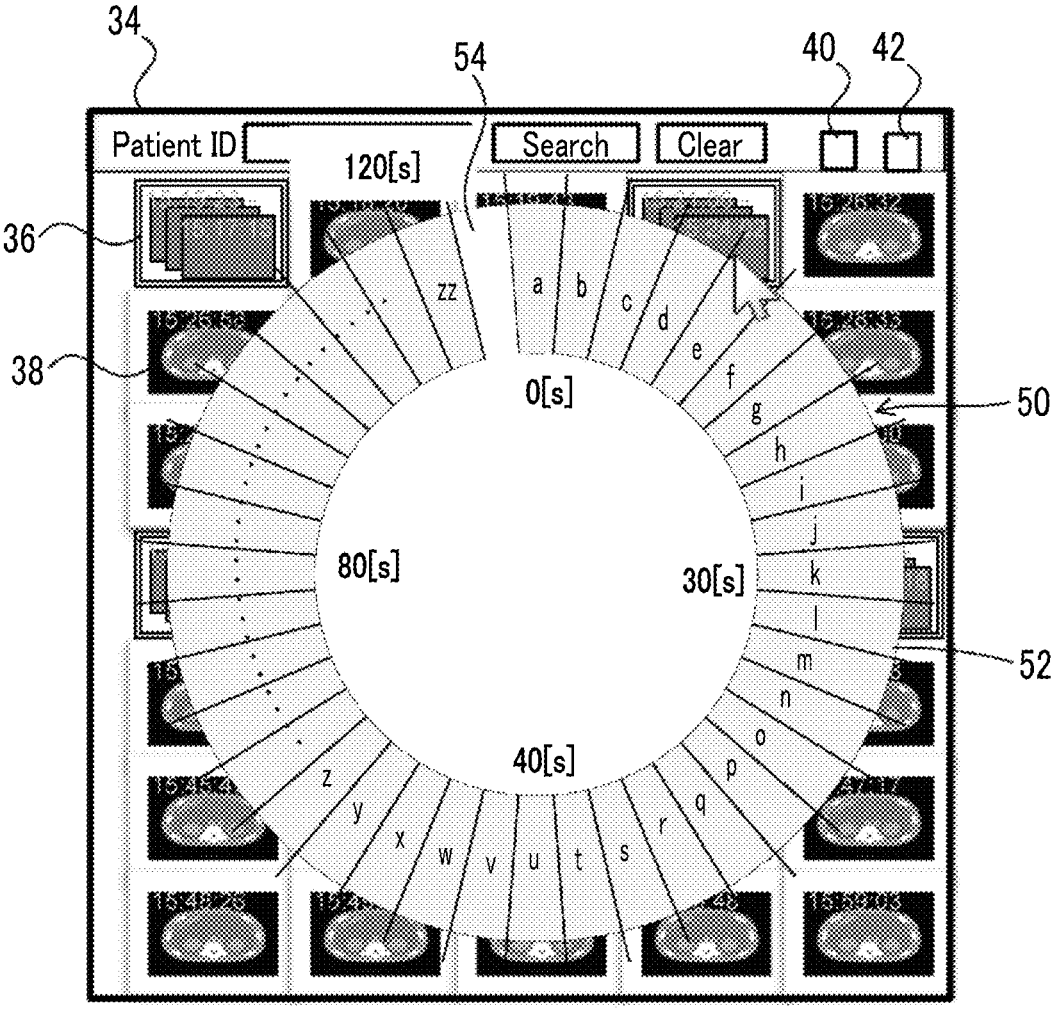
FIG. 7 is a diagram showing the import screen and a dialog.

FIG. 7 shows a dialog 50. For example, the display controller 26 displays the dialog 50 on the import screen 34. The dialog 50 is an image in which FIG. 52 respectively corresponding to the images included in the image group A selected by the user are arranged and represented in accor-dance with the order of the imaging times of the images. That is, the imaging time information is included in the accessory information of the image, and the display con-troller 26 specifies the imaging time of each image by referring to the imaging time information included in the accessory information of each image. The display controller 26 arranges and displays the FIG. 52 corresponding to the images in accordance with the order of the imaging times of the images. One FIG. 52 corresponds to an image captured at the imaging time corresponding to a position at which the FIG. 52 is disposed. For example, the display controller 26 disposes and displays the figures in an annular shape in accordance with the imaging times of the images. As a result, the dialog 50 having an annular shape is formed and displayed. For example, each FIG. 52 has a fan-like shape, and the dialog 50 is formed by arranging a plurality of FIG. 52 in an annular shape.

In the example shown in FIG. 7, for convenience of description, reference numeral a, b, c, or the like is attached to each of the FIG. 52. The FIG. 52 with the reference numeral a will be referred to as a FIG. 52*a*, and the FIG. 52 with the reference numeral b will be referred to as a FIG. 52*b*. The same applies to the figures with other reference numerals.

The FIG. 52*a* is a figure corresponding to a certain image (tentatively referred to as an image a) included in the image group A represented by the thumbnail image 48. The image a is an image captured at the earliest imaging time (that is, the earliest time phase) in the image group. The FIG. 52*b* is a figure corresponding to an image included in the image group A, and is a figure corresponding to an image (tentatively referred to as an image b) captured in the next time phase of the image a. The FIG. 52*c* is a figure corresponding to an image included in the image group A, and is a figure corresponding to an image (tentatively referred to as an image c) captured in the next time phase of the image b. For example, a character string representing the time phases (30 [s], 40 [s], and 80 [s]) is displayed in the dialog 50 with the imaging time of the image a as a reference (0 [s]). For example, in a case in which the dialog 50 is likened to a clock, the figures are disposed such that a 12 o'clock position corresponds to 0 [s] and the time phase advances clockwise.

The image a and the image b are images continuously captured at the time intervals equal to or less than the predetermined time interval. That is, a difference (imaging time interval) between the imaging time of the image a and the imaging time of the image b is the time interval equal to or less than the predetermined time interval. The image b and the image c are images continuously captured at the time intervals equal to or less than the predetermined time interval. That is, a difference (imaging time interval) between the imaging time of the image b and the imaging time of the image c is the time interval equal to or less than the predetermined time interval. The same applies to images d, e, f, and the like.

As described above, the images a, b, c, and the like are images captured in this order, and an interval between the imaging times of the images is the time interval equal to or less than the predetermined time interval.

Since the FIG. 52*a* is a figure corresponding to the first image a, the FIG. 52*a* is disposed at a position corresponding to a first time phase (0 [s]) in the dialog 50. Since the FIG. 52*b* is a figure corresponding to the image b captured next to the image a, the FIG. 52*b* is disposed next to the FIG. 52*b*. Since the FIG. 52*c* is a figure corresponding to the image c captured next to the image b, the FIG. 52*c* is disposed next to the FIG. 52*c*. The same applies to FIGS. 52*d*, 52*e*, 52*f*, and the like.

The display controller 26 may display the dialog 50 with a gap between a figure corresponding to an image having the earliest imaging time in the image group A and a figure corresponding to an image having the latest imaging time in the image group A.

In the example shown in FIG. 7, the image a is the image having the earliest imaging time in the image group A. An image zz is the image having the latest imaging time in the image group A. In this case, the display controller 26 displays the dialog 50 with a gap between the FIG. 52*a* corresponding to the image a and a FIG. 52*zz* corresponding to the image zz. For example, a gap 54 is formed between the FIG. 52*a* and the FIG. 52*zz*, and the first FIG. 52*a* and the last FIG. 52*zz* are displayed apart from each other.

By displaying the first FIG. 52*a* and the last FIG. 52*zz* apart from each other, the user can recognize the first image a and the last image zz in a distinguishable manner. That is, in a case in which the FIG. 52*a* and the FIG. 52*zz* are displayed in contact with each other, a situation occurs in which it is difficult for the user to know which figure is the figure corresponding to the first image a or which figure is the figure corresponding to the last image zz. By displaying the first FIG. 52*a* and the last FIG. 52*zz* apart from each other, it is easy for the user to know which figure is the figure corresponding to the first image a or which figure is the figure corresponding to the last image zz.

It should be noted that it is also possible to form a dialog different from the dialog 50 by arranging a plurality of rectangular figures in a band shape in a row without using the fan-like figure. In this case, in a case in which the number of images is large, it is necessary to reduce a size of the figure corresponding to one image. Therefore, it is difficult to designate a target figure via a mouse operation, a touch operation, or the like. On the other hand, with the dialog 50 having an annular shape, since a plurality of figures can be disposed in an area having a length of about 3.14 times a diameter of a circle, the size of each figure can be increased. Therefore, it is easy to designate the target figure by a mouse operation, a touch operation, or the like. In addition, with the dialog 50, a plurality of figures can be displayed on one screen without scrolling the screen. Of course, in the present embodiment, a form in which a plurality of rectangular figures are disposed in a band shape in a row is not excluded. For example, such a form may be used in a case in which the number of images is small, or such a form may be used depending on the selection of the user.

In a case in which the figure is selected on the dialog 50, the controller 24 determines the image corresponding to the selected figure as the image that is the acquisition candidate (that is, the image that is the import candidate).

Figure 8:
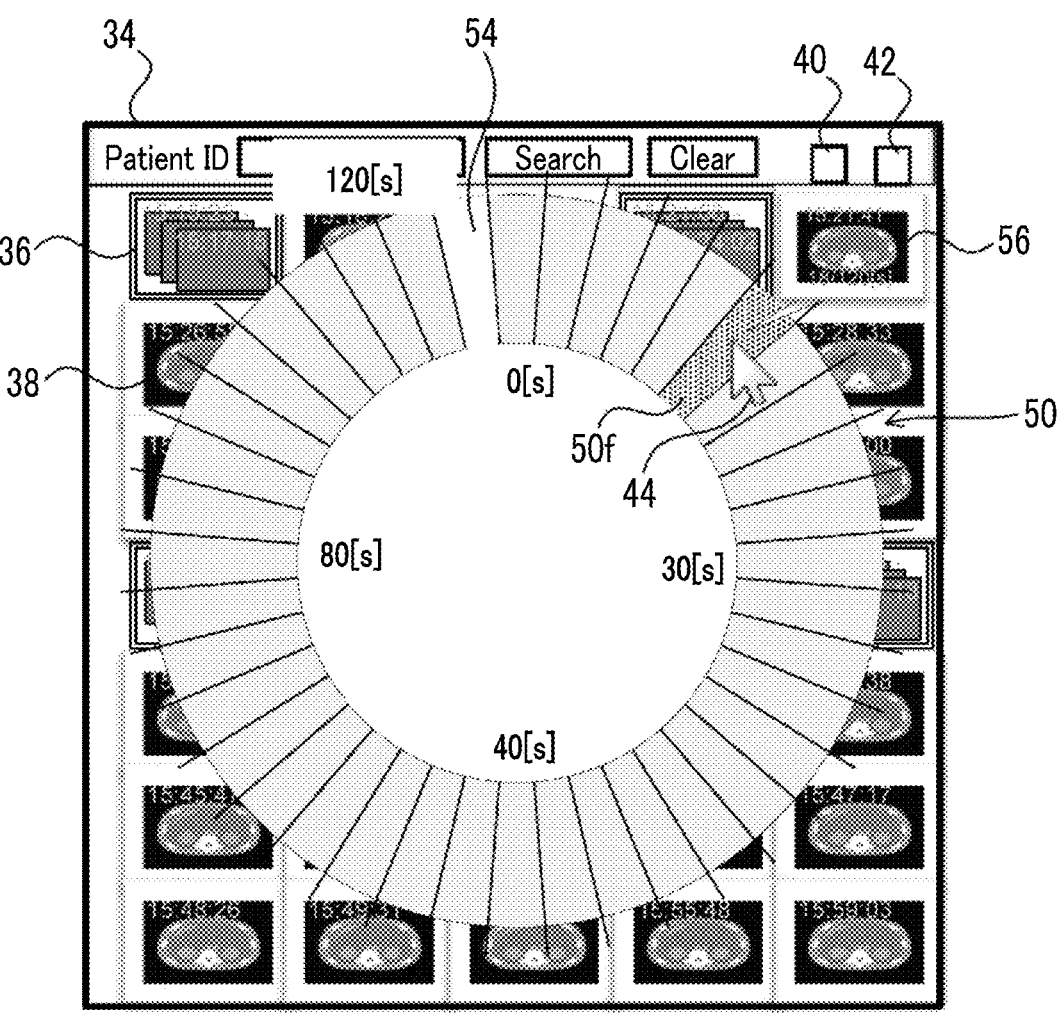
FIG. 8 is a diagram showing the import screen and the dialog.
Figure 9:
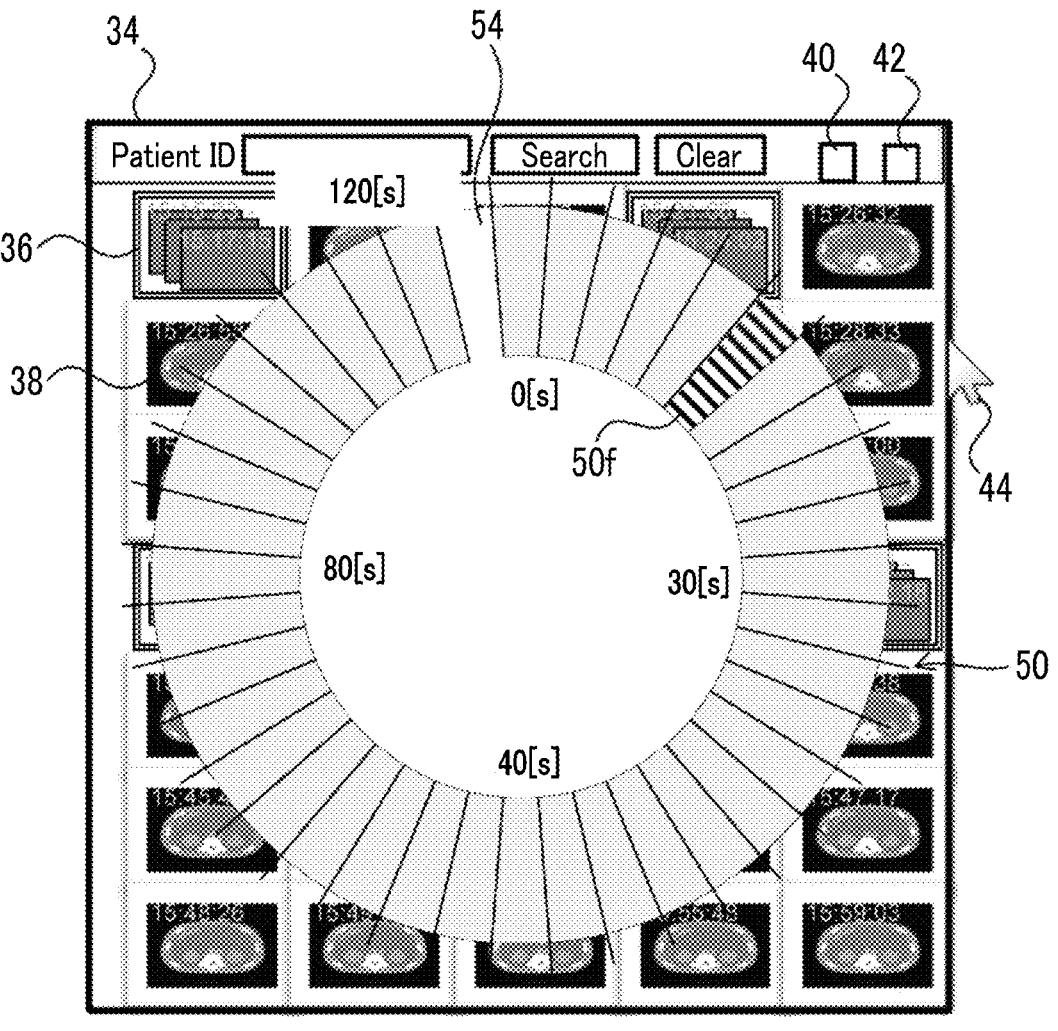
FIG. 9 is a diagram showing the import screen and the dialog.
Figure 10:
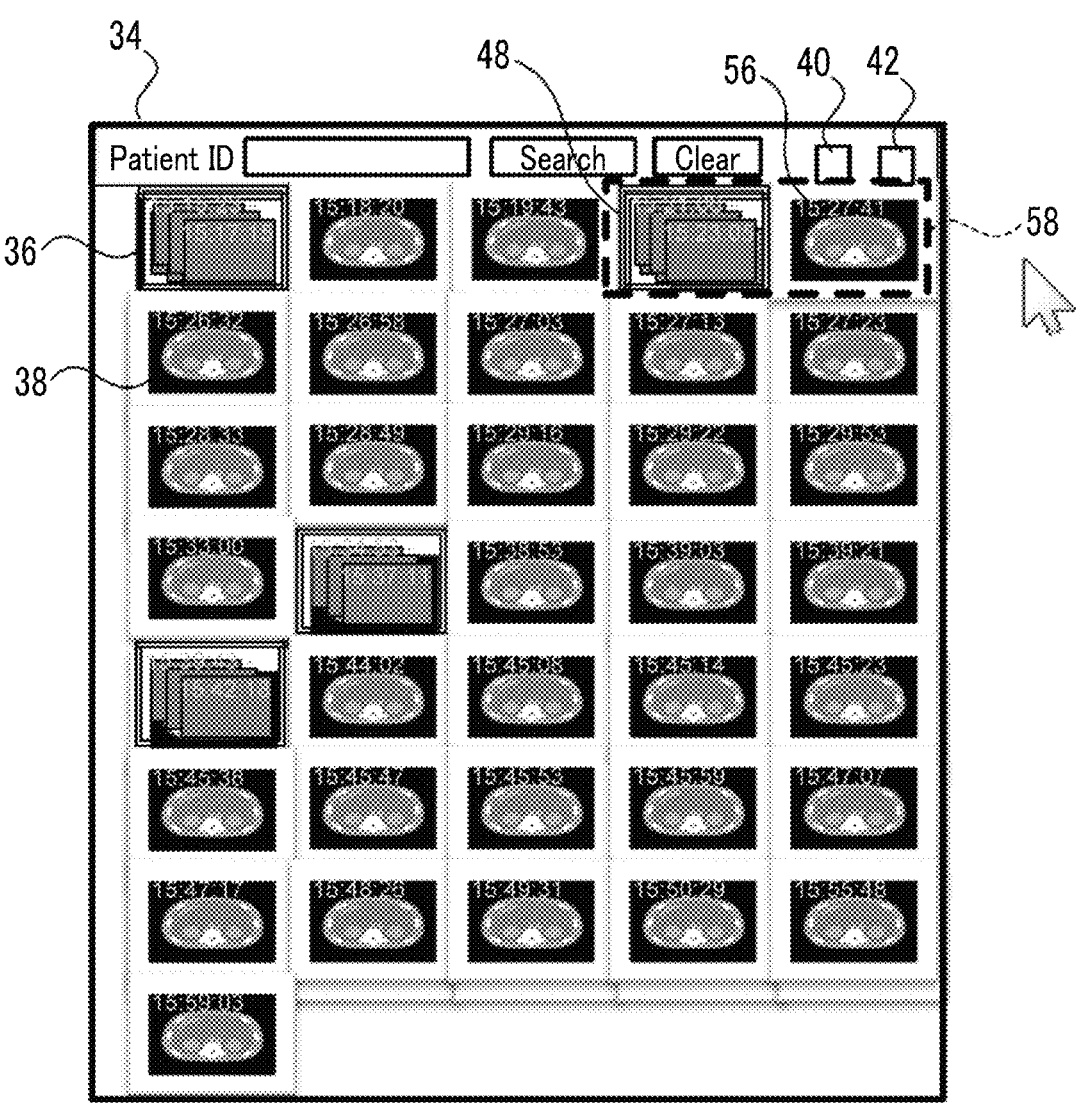
FIG. 10 is a diagram showing the import screen and the dialog.

This processing will be described in detail with reference to FIGS. 8 to 10. FIGS. 8 to 10 show the import screen 34 and the dialog 50.

For example, as shown in FIG. 8, in the dialog 50, a FIG. 50*f* is selected by the user as the figure representing the image that is the acquisition candidate. In a case in which the FIG. 50*f* is selected, the display controller 26 displays a thumbnail image 56 representing an image f corresponding to the FIG. 50*f* on the import screen 34. For example, the display controller 26 displays the thumbnail image 56 next to the FIG. 50*f*, or displays a balloon from the FIG. 50*f* to display the thumbnail image 56 in the balloon. By displaying the thumbnail image 56 in this way, the user can confirm the image f captured in the time phase corresponding to the FIG. 50*f*. That is, the user can confirm the image f that is the acquisition candidate by using the thumbnail image 56.

Next, in a case in which the user operates the operation unit 28 to designate an area other than the dialog 50, the display controller 26 closes the dialog 50. That is, the display controller 26 hides the dialog 50. For example, as shown in FIG. 9, in a case in which the user moves the pointer 44 to the area other than the dialog 50 and clicks the mouse, the display controller 26 closes the dialog 50.

The display controller 26 may change a color of the selected FIG. 50*f*. As a result, the user can recognize that the FIG. 50*f* is selected. For example, in a case in which the click or the touch operation is not performed in a state in which the pointer 44 is disposed on the FIG. 50*f* (that is, a case in which the selection of the FIG. 50*f* is not decided), as shown in FIG. 8, the display controller 26 displays the thumbnail image 56 in association with the dialog 50 on the import screen 34. In this case, the display controller 26 displays the FIG. 50*f* in a first color. Next, in a case in which the click or the touch operation is performed in a state in which the pointer 44 is disposed on the FIG. 50*f* (that is, a case in which the selection of the FIG. 50f is decided), the display controller 26 changes the color of the FIG. 50f from the first color to a second color (color different from the first color). As a result, the user can recognize that the selection of the FIG. 50f is decided, that is, that the image f corresponding to the FIG. 50f is selected as the acquisition candidate.

FIG. 10 shows the import screen 34 after the dialog 50 is closed. In a case in which the dialog 50 is closed, the display controller 26 displays, on the import screen 34, the image that is the acquisition candidate and the image group A as separate thumbnail images such that a fact that the image that is the acquisition candidate is the image belonging to the image group A is indicated.

Specifically, the display controller 26 displays, on the import screen 34, the thumbnail image 56 representing the image f (that is, the image that is the acquisition candidate) corresponding to the FIG. 50f selected on the dialog 50 as a thumbnail image different from the thumbnail image 48 representing the image group A. In this case, the display controller 26 displays the thumbnail image 56 representing the image f next to the thumbnail image 48 representing the image group A.

In addition, the display controller 26 displays, on the import screen 34, a frame 58 surrounding the thumbnail image 56 of the image f and the thumbnail image 48 of the image group A such that a fact that the image f that is the acquisition candidate is the image belonging to the image group A represented by the thumbnail image 48 is indicated. By surrounding the thumbnail images 48 and 56 with the frame 58 in this way, the user can recognize that the image f is the image belonging to the original image group A. In addition, since the thumbnail image 56 of the image f is displayed as the thumbnail image different from the thumbnail image 48 of the image group A, the user can recognize that the image f is the image that is the acquisition candidate.

In a case in which the original image group A is displayed as one thumbnail image 48 after the image f that is the acquisition candidate is determined, the display controller 26 separately displays the thumbnail image 56 of the image f and the thumbnail image 48 of the image group A, and displays the frame 58 surrounding the thumbnail images 48 and 56 on the import screen 34 such that a fact that the image f is the image belonging to the image group A is indicated.

As shown in FIG. 10, in a case in which the thumbnail image 56 representing the image f that is the acquisition candidate is displayed on the import screen 34 and the thumbnail image 56 is selected by the user, the controller 24 may determine the image f that is the acquisition candidate corresponding to the selected thumbnail image 56 as an image that is not the acquisition candidate. For example, in a case in which the user selects the thumbnail image 56 by using the pointer 44 (for example, in a case in which the user clicks the thumbnail image 56), the controller 24 excludes the image f from the image that is the acquisition candidate. In this way, the selection of the image that is the acquisition candidate may be canceled on the import screen 34. In this case, the display controller 26 hides the thumbnail image 56 representing the image f and the frame 58.

Figure 11:
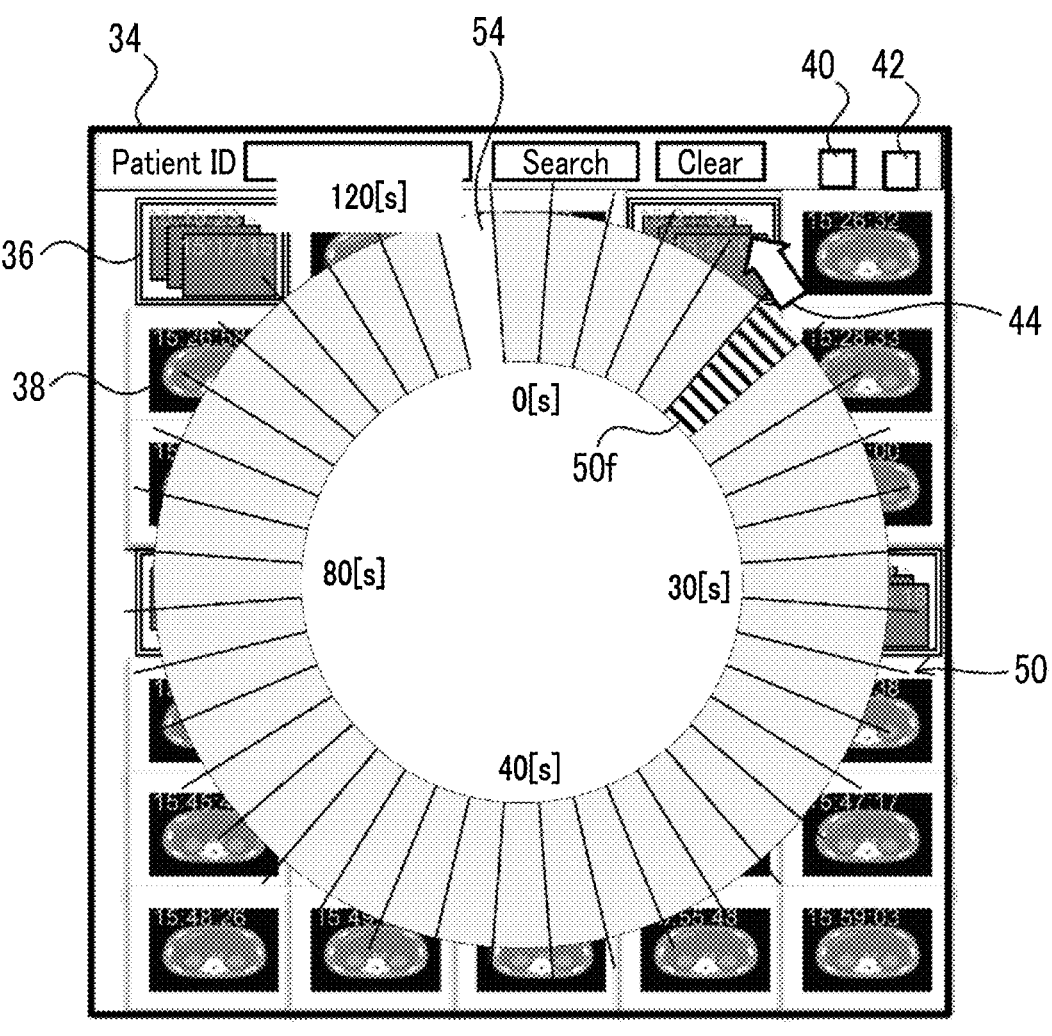
FIG. 11 is a diagram showing the import screen and the dialog.

In a case in which the user selects the thumbnail image representing the image group again on the import screen 34, the display controller 26 displays the dialog 50. For example, in a case in which the thumbnail image 48 representing the image group A is selected by the user, as shown in FIG. 11, the display controller 26 displays, on the display unit 20, the dialog 50 for selecting the image that is the acquisition candidate from the image group A.

In this stage, since the FIG. 50f is already selected by the user, the display controller 26 displays the FIG. 50f in a color indicating that the FIG. 50f is already selected.

Figure 12:
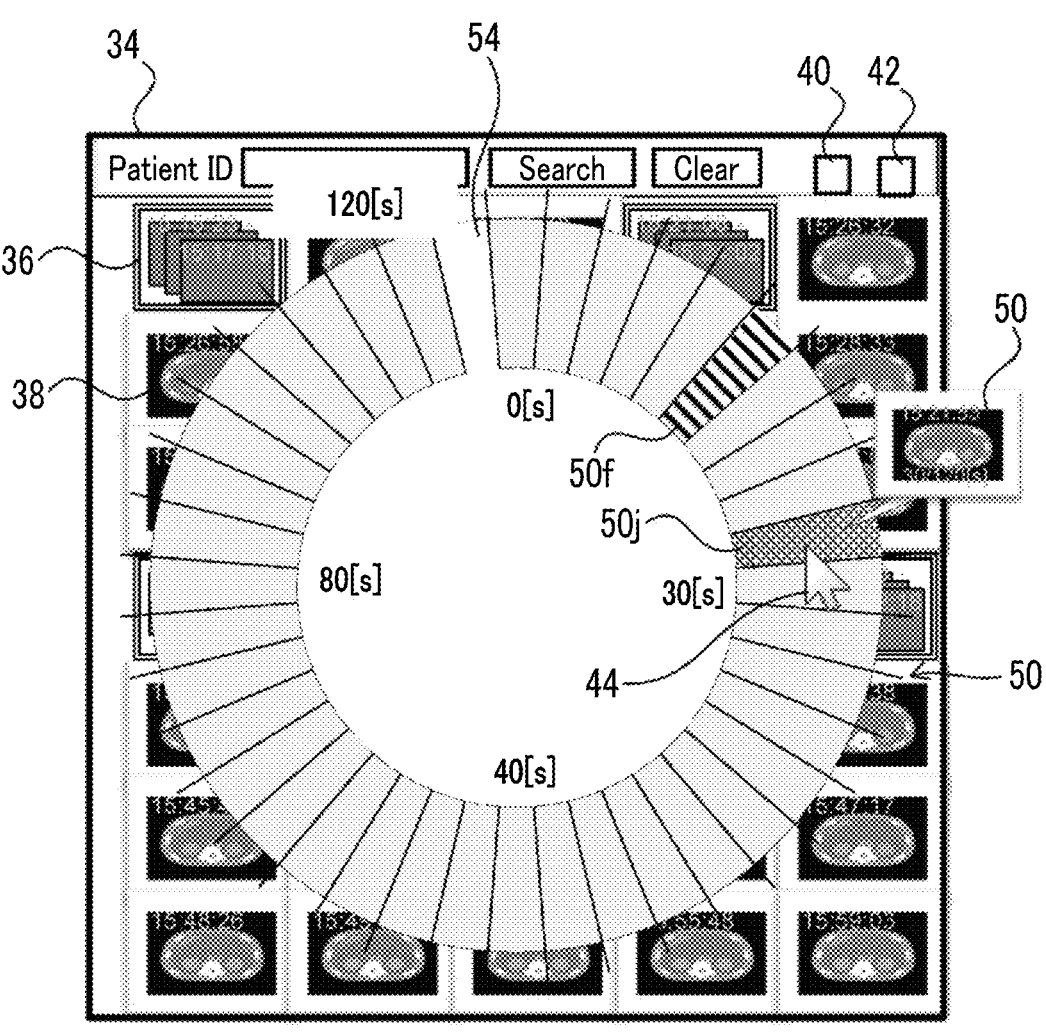
FIG. 12 is a diagram showing the import screen and the dialog.

For example, as shown in FIG. 12, in the dialog 50, in a case in which a FIG. 50j is selected by the user, the display controller 26 displays a thumbnail image 60 representing an image j corresponding to the FIG. 50j on the import screen 34. In addition, the display controller 26 changes a color of the selected FIG. 50j. These pieces of processing are the same as the pieces of processing described with reference to FIG. 8.

Figure 13:
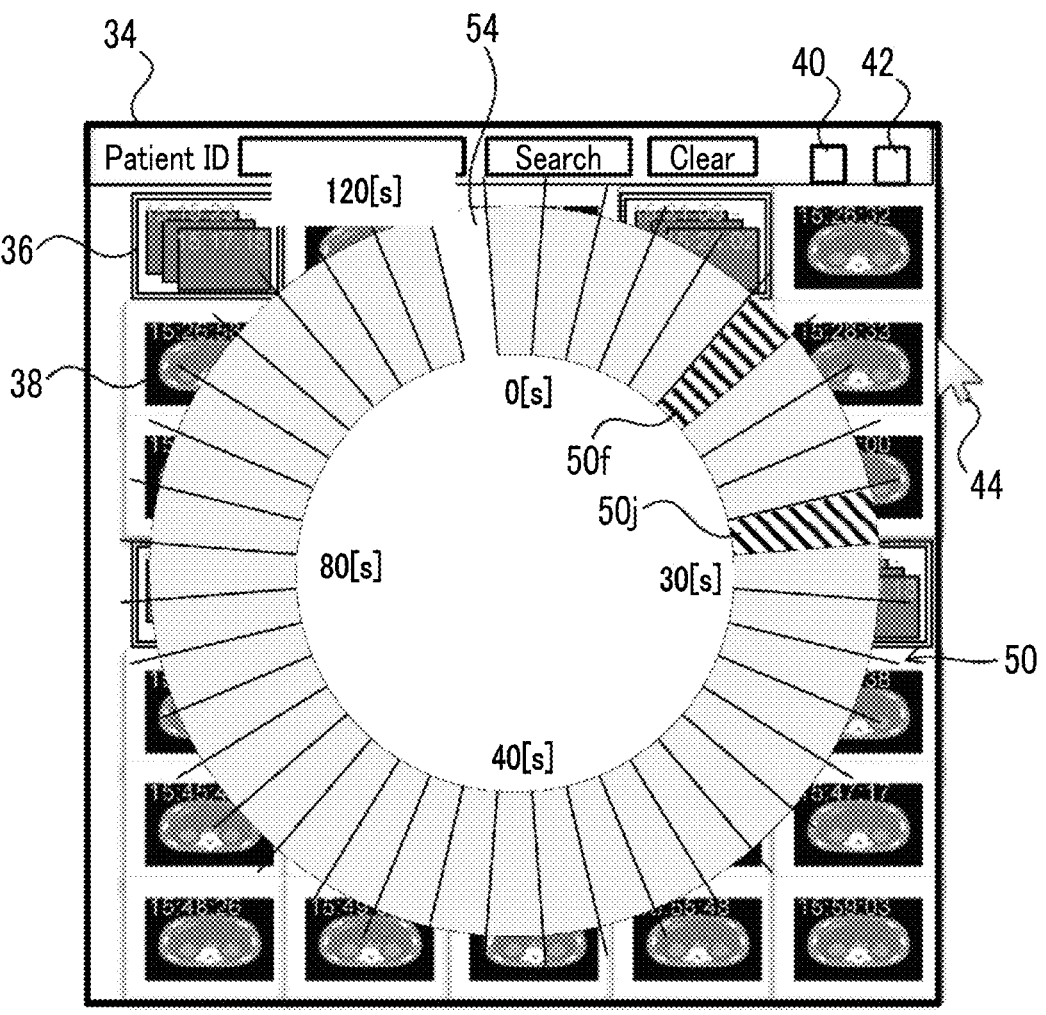
FIG. 13 is a diagram showing the import screen and the dialog.

Next, in a case in which the user designates the area other than the dialog 50, the display controller 26 closes the dialog 50. For example, as shown in FIG. 13, in a case in which the user moves the pointer 44 to the area other than the dialog 50 and clicks the mouse, the display controller 26 closes the dialog 50.

Figure 14:
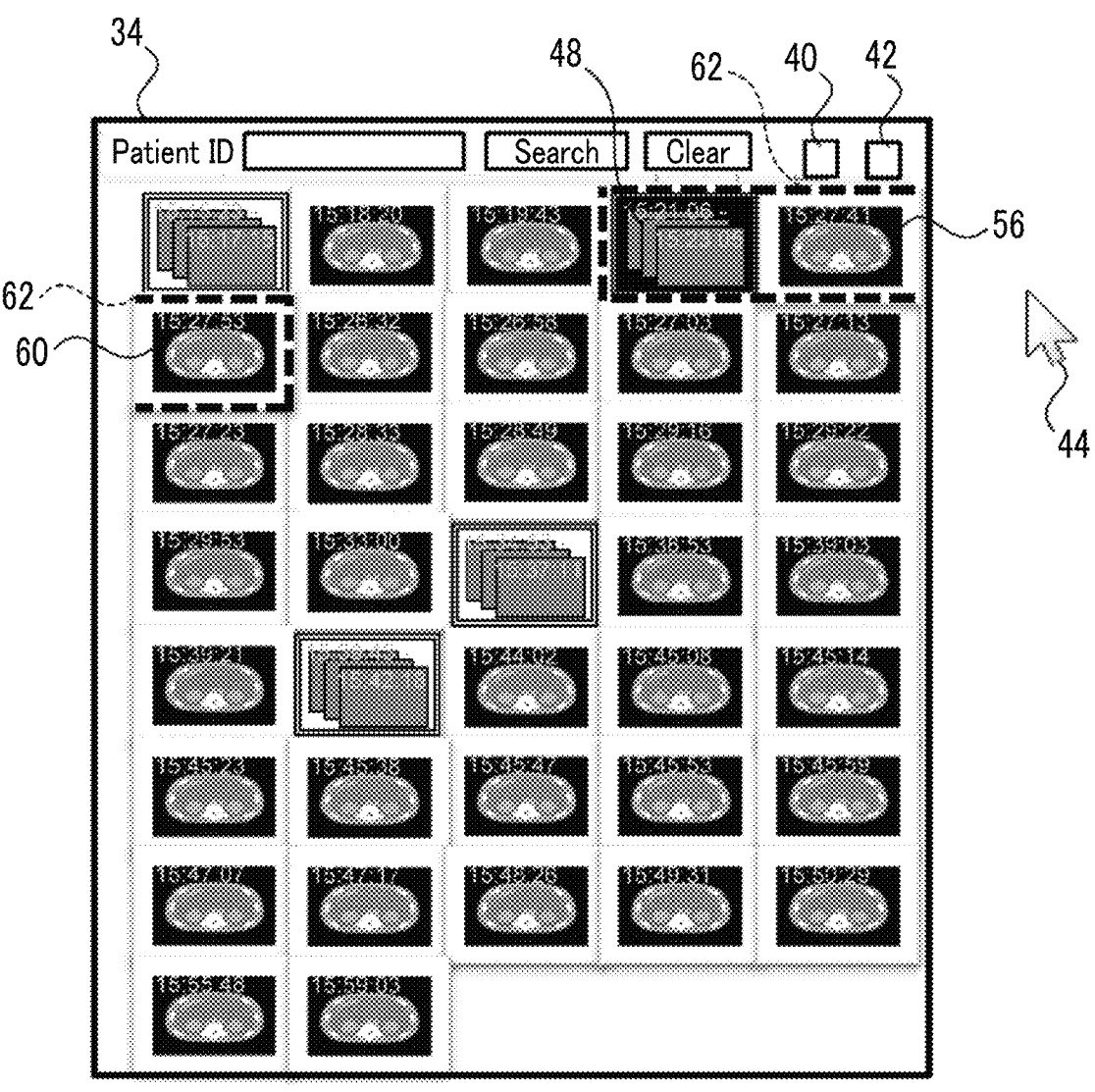
FIG. 14 is a diagram showing the import screen.

FIG. 14 shows the import screen 34 after the dialog 50 is closed. In a case in which the dialog 50 is closed, as in the example shown in FIG. 10, the display controller 26 displays, on the import screen 34, the image that is the acquisition candidate and the image group A as separate thumbnail images such that a fact that the image that is the acquisition candidate is the image belonging to the image group A is indicated.

Specifically, the display controller 26 displays, on the import screen 34, the thumbnail image 56 representing the image f corresponding to the FIG. 50f already selected on the dialog 50 the thumbnail image 60 representing the image j corresponding to the FIG. 50j newly selected on the dialog 50 as thumbnail images different from the thumbnail image 48 representing the image group A. In this case, the display controller 26 displays the thumbnail image 56 representing the previously selected image f next to the thumbnail image 48 representing the image group A, and displays the thumbnail image 60 representing the newly selected image j next to the thumbnail image 56. In the example shown in FIG. 14, since there is no space next to the thumbnail image 56, the thumbnail image 60 is displayed in one column below the thumbnail image 56.

In addition, the display controller 26 displays, on the import screen 34, a frame 62 surrounding the thumbnail image 56 of the image f, the thumbnail image 60 of the image j, and the thumbnail image 48 of the image group A such that a fact that the images f and j are the images belonging to the image group A represented by the thumbnail image 48 is indicated. In the example shown in FIG. 14, since the thumbnail image 60 is displayed in one column below the thumbnail images 48 and 56, the frame 62 is also displayed over two columns. By surrounding the thumbnail images 48, 56, and 60 with the frame 62 in this way, the user can recognize that the images f and j are the images belonging to the original image group A. In addition, the user can recognize that the images f and j are the images that are the acquisition candidates.

In a case in which the user presses the import button in a state in which the images f and j are selected as the images that are the acquisition candidates, the acquisition unit 30 imports the images f and j that are the import candidates from the image server 200 into the ultrasound diagnostic apparatus 10. The storage unit 22 of the ultrasound diagnostic apparatus 10 stores the images f and j. Further, the imported images f and j are registered in the database constructed by the ultrasound diagnostic apparatus 10.

Figure 15:
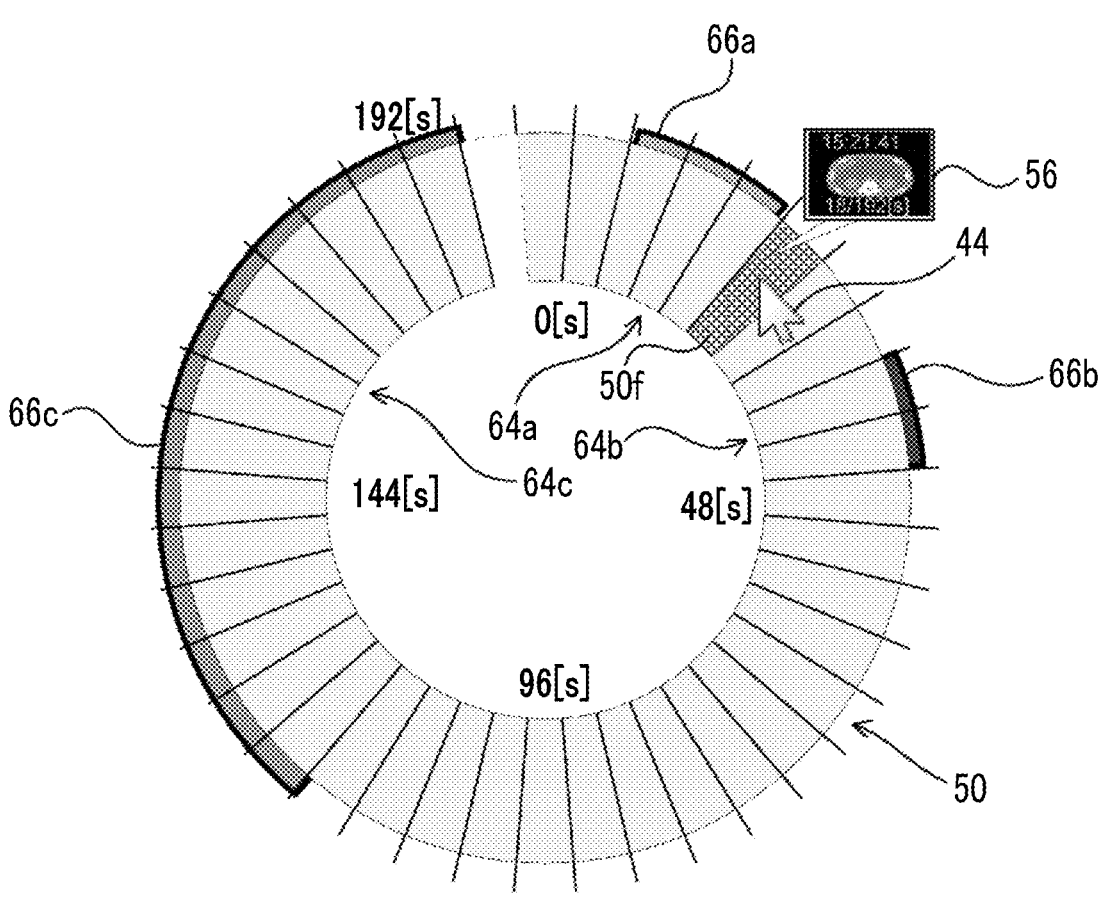
FIG. 15 is a diagram showing the dialog.

A modification example of the dialog 50 will be described below with reference to FIG. 15. FIG. 15 shows the dialog 50.

In the modification example, based on a timing at which the contrast medium flows in a specific part of the subject, the display controller 26 displays, in the dialog 50, a figure corresponding to an image captured at the timing in a distinguishable manner from figures corresponding to other images. For example, the display controller 26 highlights and displays the figure corresponding to the image captured at the timing at which the contrast medium flows in. In this way, the image that is the import candidate may be recommended to the user.

For example, a time required from the time when the contrast medium is injected into the patient that is the subject until the contrast medium flows in each part is presumed in advance based on an empirical rule, a model, or the like. The controller 24 presumes the imaging time during which the contrast medium flows in, for each part of the subject, based on an elapsed time from the time when the contrast medium is injected into the patient and the time required for the contrast medium to flow in each part. In other words, the controller 24 presumes the part in which the contrast medium flows in, for each imaging time, based on the elapsed time from the time when the contrast medium is injected into the patient and the time required for the contrast medium to flow in each part. That is, the controller 24 specifies an image representing a part in which the contrast medium is presumed to flow in.

The display controller 26 displays, in the dialog 50, the figure corresponding to the image captured at the timing at which the contrast medium is presumed to flow in a distinguishable manner from the figures corresponding to other images (that is, an image captured at the timing at which the contrast medium is not presumed to flow in).

For example, the display controller 26 changes a height or a color of the figure corresponding to the image captured at the timing at which the contrast medium is presumed to flow in.

In the example shown in FIG. 15, figure groups 64a, 64b, and 64c are figure groups corresponding to the images in which the contrast medium is presumed to flow in. As indicated by reference numeral 66a, the display controller 26 displays the figure group 64a by setting the height of each figure included in the figure group 64a to be higher than the heights of other figures not included in the figure groups 64a, 64b, and 64c. The same applies to the figures included in the figure groups 64b and 64c.

The display controller 26 may change the colors of all or a part of the figures included in each of the figure groups 64a, 64b, and 64c. For example, the display controller 26 displays, in different colors, a part of the figures included in the figure group 64a, a part of the figures included in the figure group 64b, and a part of the figures included in the figure group 64c. In the example shown in FIG. 15, the display controller 26 displays, in different colors, a color of a portion indicated by reference numeral 66a, a color of a portion indicated by reference numeral 66b, and a color of a portion indicated by reference numeral 66c.

As another example, the display controller 26 may highlight and display the figure in accordance with the accessory information of the image. For example, in the image diagnostic apparatus 100 or the ultrasound diagnostic apparatus 10, various types of information may be included in the accessory information depending on the user. The display controller 26 may change the size, the shape, and the color of the figure in accordance with a content indicated by the accessory information.

The signal processing unit 16, the display processing unit 18, the controller 24, the display controller 26, the acquisition unit 30, and the identification unit 32 can be realized by using, for example, hardware resources, such as a processor and an electronic circuit, and a device, such as a memory, may be used in the realization as necessary. In addition, the signal processing unit 16, the display processing unit 18, the controller 24, the display controller 26, the acquisition unit 30, and the identification unit 32 may be realized by, for example, a computer. That is, all or a part of the signal processing unit 16, the display processing unit 18, the controller 24, the display controller 26, the acquisition unit 30, and the identification unit 32 may be realized by cooperation between hardware resources, such as a central processing unit (CPU) or a memory included in a computer, and software (program) that defines the operation of the CPU or the like. The program is stored in the storage unit 22 of the ultrasound diagnostic apparatus 10 or other storage device through a recording medium, such as a CD or a DVD, or a communication path, such as a network. As another example, the signal processing unit 16, the display processing unit 18, the controller 24, the display controller 26, the acquisition unit 30, and the identification unit 32 may be realized by a digital signal processor (DSP), an application specific integrated circuit (ASIC), a field programmable gate array (FPGA), or the like. Of course, a graphics processing unit (GPU) and the like may be used. The signal processing unit 16, the display processing unit 18, the controller 24, the display controller 26, the acquisition unit 30, and the identification unit 32 may be realized by a single apparatus, and each of the functions of the signal processing unit 16, the display processing unit 18, the controller 24, the display controller 26, the acquisition unit 30, and the identification unit 32 may be realized by one or more apparatuses.

The present embodiment may be applied to, for example, real-time virtual sonography (RVS). That is, the display controller 26 of the ultrasound diagnostic apparatus 10 may synchronize the ultrasound image generated by the ultrasound diagnostic apparatus 10 with the image acquired from the image diagnostic apparatus 100 or the image server 200 to simultaneously display both the images on the display. According to the present embodiment, in the execution of the RVS, it is possible to quickly and easily select the image that is the import candidate. For example, for the RVS, an image captured in a target time phase can be quickly and easily selected as the image that is the import candidate.

It should be noted that, in the embodiment described above, a case is described in which the ultrasound diagnostic apparatus 10 acquires the image, but even in a case in which the image diagnostic apparatus 100 other than the ultrasound diagnostic apparatus 10 acquires the image, the same processing as in a case in which the ultrasound diagnostic apparatus 10 acquires the image is executed. For example, a function related to the image acquisition of the controller 24, the display controller 26, the acquisition unit 30, and the identification unit 32 may be provided in the image diagnostic apparatus 100, and the image diagnostic apparatus 100 may display the dialog to acquire the image according to the embodiment.

What is claimed is:
1. An ultrasound diagnostic apparatus comprising:
a program storage device tangibly embodying one or more programs of executable instructions; and
one or more processors configured via execution of the one or more programs to:
collect image data for a contrast examination;
identify, in connection with the image data collected for the contrast examination and as one image group, plural images continuously captured at time intervals equal to or less than a predetermined time interval among a plurality of images captured by an image diagnostic apparatus; and control to display, on a display, the image group and an image other than the image group in a distinguishable manner, for the contrast examination.

2. The ultrasound diagnostic apparatus according to claim 1, wherein the one or more processors configured via execution of the one or more programs identify the image group by assuming that the images included in the image group are images generated by imaging a subject using a contrast medium.

3. The ultrasound diagnostic apparatus according to claim 2, wherein the one or more processors configured via execution of the one or more programs control to display, on the display, the image group as one thumbnail image.

4. The ultrasound diagnostic apparatus according to claim 3, wherein, in a case in which the thumbnail image representing the image group is selected by a user, the one or more processors configured via execution of the one or more programs control to display, on the display, a dialog for selecting an image that is an acquisition candidate, the dialog is an image in which figures respectively corresponding to the images included in the image group are arranged and represented in accordance with an order of imaging times of the images, and in a case in which the figure is selected on the dialog, the one or more processors configured via execution of the one or more programs determine the image corresponding to the selected figure as the image that is the acquisition candidate.

5. The ultrasound diagnostic apparatus according to claim 4, wherein, in a case in which the image group is displayed as one thumbnail image after the image that is the acquisition candidate is determined, the one or more processors configured via execution of the one or more programs control to display, on the display, the image that is the acquisition candidate and the image group as separate thumbnail images such that a fact that the image that is the acquisition candidate is an image belonging to the image group is indicated.

6. The ultrasound diagnostic apparatus according to claim 5, wherein, in a case in which a thumbnail image representing the image that is the acquisition candidate is displayed on the display and the thumbnail image representing the image that is the acquisition candidate is selected, the one or more processors configured via execution of the one or more programs determine the image that is the acquisition candidate corresponding to the selected thumbnail image as an image that is not the acquisition candidate.

7. The ultrasound diagnostic apparatus according to claim 4, wherein the dialog has a shape in which the figures are disposed in an annular shape in accordance with the imaging times of the images.

8. The ultrasound diagnostic apparatus according to claim 7, wherein the one or more processors configured via execution of the one or more programs control dispose the figures with a gap between a figure corresponding to an image having an earliest imaging time in the image group and a figure corresponding to an image having a latest imaging time in the image group.

9. The ultrasound diagnostic apparatus according to claim 8, wherein, based on a timing at which the contrast medium flows in a specific part of the subject, the one or more processors configured via execution of the one or more programs control to display, in the dialog, a figure corresponding to an image captured at the timing in a distinguishable manner from figures corresponding to other images.

10. A computer-readable recording medium recording a program of executable instruction for causing a computer to:

collect image data for a contrast examination;

identify, in connection with the image data collected for the contrast examination and as one image group, plural images continuously captured at time intervals equal to or less than a predetermined time interval among a plurality of images captured by an image diagnostic apparatus; and control to display, on a display, the image group and an image other than the image group in a distinguishable manner, for the contrast examination.

\* \* \* \* \*